(12) United States Patent
Soltis et al.

(10) Patent No.: US 7,725,197 B2
(45) Date of Patent: May 25, 2010

(54) MEDICAL ELECTRICAL LEAD WITH FRICTION-ENHANCING FIXATION FEATURES

(75) Inventors: Brian D. Soltis, St. Paul, MN (US); Bruce A. Tockman, Scandia, MN (US); Kent C. B. Stalker, San Marcos, CA (US); Eric T. Johnson, Temecula, CA (US); Peter J. D'Aquanni, Murrieta, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 981 days.

(21) Appl. No.: 11/424,349

(22) Filed: Jun. 15, 2006

(65) Prior Publication Data

US 2007/0293922 A1    Dec. 20, 2007

(51) Int. Cl.
*A61N 1/05* (2006.01)
(52) U.S. Cl. .................................... 607/129; 607/122
(58) Field of Classification Search ........................ None
See application file for complete search history.

(56) References Cited

U.S. PATENT DOCUMENTS

| | | | |
|---|---|---|---|
| 4,280,514 A | 7/1981 | MacGregor | |
| 4,550,737 A | 11/1985 | Osypka | |
| 5,318,572 A | 6/1994 | Helland et al. | |
| 5,387,233 A | 2/1995 | Alferness et al. | |
| 5,476,498 A | 12/1995 | Ayers | |
| 5,531,781 A | 7/1996 | Alferness et al. | |
| 5,628,779 A | 5/1997 | Bornzin et al. | |
| 5,865,843 A | 2/1999 | Baudino | |
| 5,931,864 A | 8/1999 | Chastain et al. | |
| 6,083,247 A | 7/2000 | Rutten et al. | |
| 6,129,750 A | 10/2000 | Tockman et al. | |
| 6,263,249 B1 | 7/2001 | Stewart et al. | |
| 6,263,250 B1 | 7/2001 | Skinner | |
| 6,301,507 B1 | 10/2001 | Bakels et al. | |
| 6,363,286 B1 | 3/2002 | Zhu et al. | |
| 6,408,213 B1 | 6/2002 | Bartig et al. | |
| 6,584,363 B2 | 6/2003 | Heil, Jr. et al. | |
| 6,772,015 B2 | 8/2004 | Dahl et al. | |
| 6,792,318 B2 | 9/2004 | Chitre et al. | |
| 6,961,621 B2 | 11/2005 | Krishnan et al. | |
| 7,319,905 B1 * | 1/2008 | Morgan et al. | 607/129 |
| 2003/0050681 A1 | 3/2003 | Pianca et al. | |
| 2003/0105506 A1 | 6/2003 | Krishnan et al. | |
| 2003/0109914 A1 | 6/2003 | Westlund et al. | |
| 2003/0199962 A1 | 10/2003 | Struble et al. | |
| 2003/0220676 A1 | 11/2003 | Helland | |
| 2003/0220677 A1 | 11/2003 | Doan et al. | |
| 2004/0059402 A1 | 3/2004 | Soukup et al. | |

(Continued)

*Primary Examiner*—Carl H. Layno
*Assistant Examiner*—Jon-Eric C. Morales
(74) *Attorney, Agent, or Firm*—Faegre & Benson LLP

(57) ABSTRACT

Medical electrical leads are provided including fixation features for acute and chronic fixation of a portion of the respective leads within the cardiac venous system. The medical electrical lead includes an elongate body having proximal and distal regions. Tissue contacting portions are selectively located in the distal region to contact an inner surface of the cardiac vessel when the lead is in an implanted position. The tissue contacting portion(s) include fixation features adapted to frictionally engage the inner surface of the cardiac vessel and promote tissue in-growth for chronic fixation. In some embodiments, the fixation features are detachable from the lead such that the lead can be extracted from its implanted position after tissue in-growth occurs.

17 Claims, 7 Drawing Sheets

U.S. PATENT DOCUMENTS

2004/0230279 A1 11/2004 Cates et al.
2004/0243210 A1 12/2004 Morgan et al.
2005/0171588 A1 8/2005 Wahlstrom et al.

* cited by examiner

MEDICAL ELECTRICAL LEAD WITH FRICTION-ENHANCING FIXATION FEATURES

TECHNICAL FIELD

The present invention relates to devices and methods for fixation of medical electrical leads. In particular, the present invention is directed to a medical electrical lead including fixation features providing enhanced frictional engagement for fixation of a portion of the lead within a cardiac vessel.

BACKGROUND

Implantable medical devices for treating irregular contractions of the heart with electrical stimuli are known. Exemplary implantable devices are defibrillators and pacemakers. Various types of electrical leads for defibrillators and pacemakers have been suggested, many of which are placed transvenously. Such leads are introduced into the patient's vasculature at a venous access site and travel through veins to the sites where the leads' electrodes will be implanted or otherwise contact target coronary tissue. Electrodes for transvenously-placed leads can be implanted in the endocardium (the tissue lining the inside of the heart) of the right atrium or ventricle, or alternatively, in the branch vessels of the coronary venous system. In particular, lead electrodes can be implanted in the coronary sinus or a branch vessel thereof for sensing and/or stimulation of the left side of the heart (i.e., the left ventricle).

Various techniques have been used to facilitate fixation of the foregoing types of leads at the desired implantation sites. For leads partially implanted within the coronary venous system, fixation techniques should provide both acute and chronic fixation for withstanding natural heart motion and retrograde blood flow which naturally tend to push the lead out of its implanted position. Additionally, it is desirable to permit and facilitate partial or complete removal of the lead and fixation structures after implantation if necessary or desired.

There is thus a need for devices and methods for fixation of cardiac leads within the coronary vasculature which provides both acute and chronic fixation yet still permits removal of the leads as desired.

SUMMARY

The present invention, in one embodiment, is a medical electrical lead configured to be partially implanted in a cardiac vessel. The lead comprises an elongate body defining a proximal region and a distal region. The proximal region includes a proximal end adapted to be connected to an implantable medical device. The distal region includes at least one tissue contacting portion selectively located to contact an inner surface of the cardiac vessel when the distal region is located in the cardiac vessel. The distal region further includes a fixation feature coupled to the tissue contacting portion, the fixation feature including a fabric structure adapted to frictionally engage the inner surface of the cardiac vessel and to allow tissue in-growth.

The present invention, in another embodiment, is a medical electrical lead configured to be partially implanted in a cardiac vessel, the lead comprising an elongate body defining a proximal region and a distal region. The proximal region includes a proximal end adapted to be connected to an implantable medical device. The distal region including at least one tissue contacting portion selectively located to contact an inner surface of the cardiac vessel when the distal region is located in the cardiac vessel, and fixation means releasably coupled to the lead body in the tissue contacting portion for engaging the cardiac vessel wall and allowing tissue in-growth.

In yet another embodiment, the present invention is a medical electrical lead configured to be partially implanted in a cardiac vessel, the lead comprising an elongate body defining a proximal region and a distal region. The proximal region includes a proximal end adapted to be connected to an implantable medical device. The distal region includes at least one tissue contacting portion selectively located to contact an inner surface of the cardiac vessel when the distal region is located in the cardiac vessel, and a fixation feature on the lead body in the tissue contacting portion. The fixation feature includes a plurality of filaments extending radially outward from the lead body. The filaments are adapted to frictionally engage the cardiac vessel wall and are spaced apart on the lead body so as to enable tissue in-growth between individual filaments.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
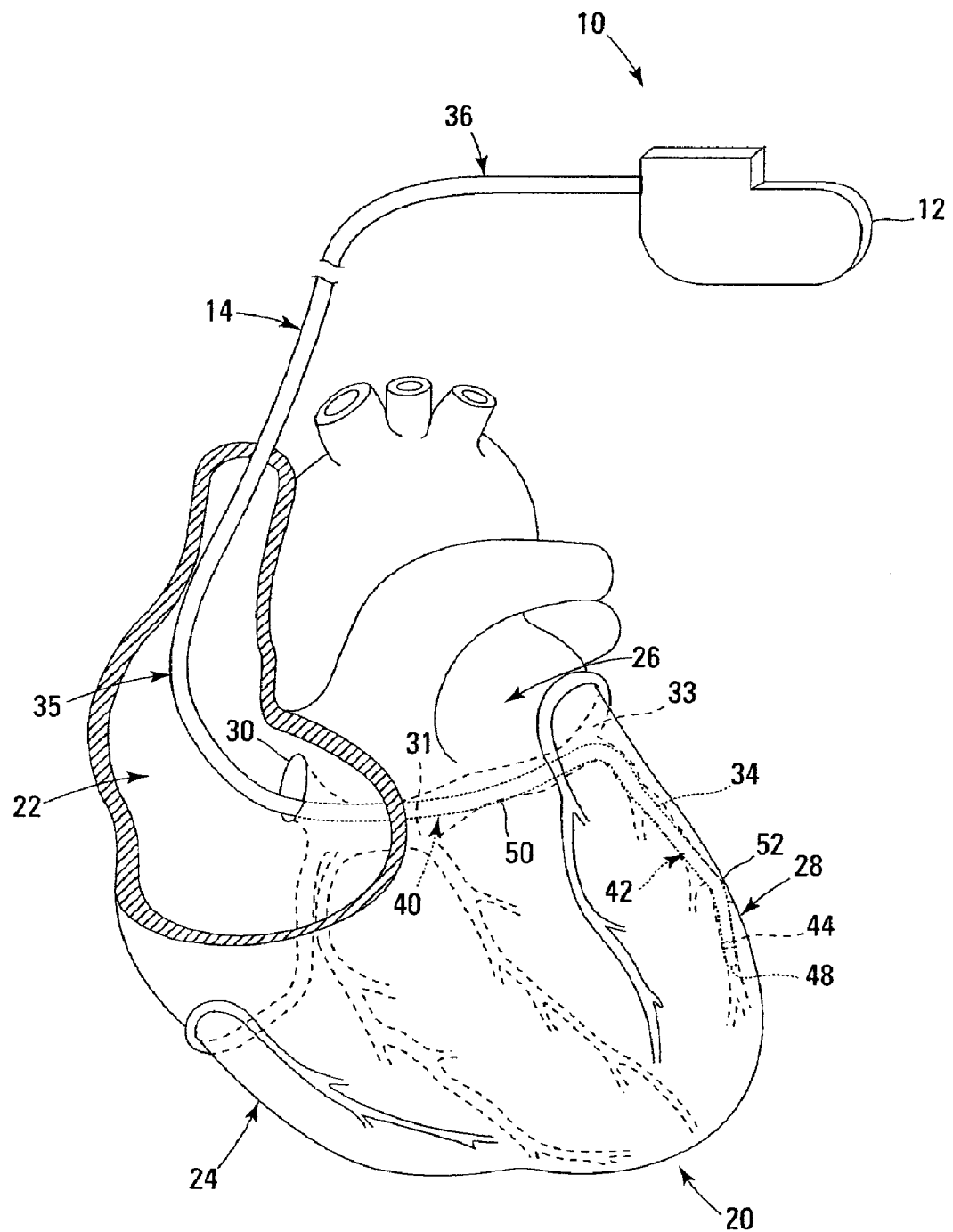
FIG. 1 is a schematic drawing of a cardiac rhythm management system including a pulse generator coupled to a lead deployed in a patient's heart according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic drawing of a cardiac rhythm management system 10 including a pulse generator 12 coupled to a lead 14 deployed in a patient's heart 20, which includes a right atrium 22 and a right ventricle 24, a left atrium 26 and a left ventricle 28, a coronary sinus ostium 30 in the right atrium 22, a coronary sinus 31, and various coronary veins including a great cardiac vein 33 and other branch vessels off the coronary sinus 31 including an exemplary branch vessel 34.

As shown in FIG. 1, the lead 14 includes an elongate body 35 defining a proximal region 36 and a distal region 40. The distal region 40 has a distal end portion 42 including at least one electrode 44 and terminating in a distal tip 48. In the embodiment illustrated in FIG. 1, the distal region 40 extends through the right atrium 22, the coronary sinus ostium 30, and the coronary sinus 31, and into the branch vessel 34 of the coronary sinus 31, with the distal end 42, and thus the electrode 44 and the distal tip 48, positioned within the branch vessel 34. The illustrated position of the lead 14 may be used, for example, for sensing physiologic parameters and delivering a pacing and/or defibrillation stimulus to the left side of the heart 20. Additionally, it will be appreciated that the lead 14 may also be partially deployed in other cardiac vessels such as the great cardiac vein 33 or other branch vessels for providing therapy to the left side of the heart 20.

The distal region 40 includes tissue contacting portions 50, 52 on the lead body 35 strategically located and adapted to contact cardiac tissue, such as, in the illustrated embodiment, interior surfaces of the coronary sinus 31 and the branch vessel 34, respectively, for fixation of the lead in the implanted position. These tissue contacting portions 50, 52 include one or more fixation features adapted to engage the interior surface of the cardiac vessel(s) to prevent, or substantially impede, spontaneous displacement and dislodgement of the lead 14 from the implanted position. These fixation features, as will be described in detail below, are adapted to provide acute fixation of the respective leads by frictionally engaging the cardiac vessel tissue. In addition, in some embodiments, the fixation features may be adapted to provide chronic fixation by promoting tissue in-growth. In still other embodiments, the fixation features may be adapted to provide both acute and chronic fixation, yet be detachable from the respective lead body to permit repositioning and/or removal of the lead if appropriate.

It will be appreciated that the lead 14 is amenable for implantation in any of the cardiac vessels, including the coronary sinus 31, the great cardiac vein 33, and other branch vessels.

Figure 2:
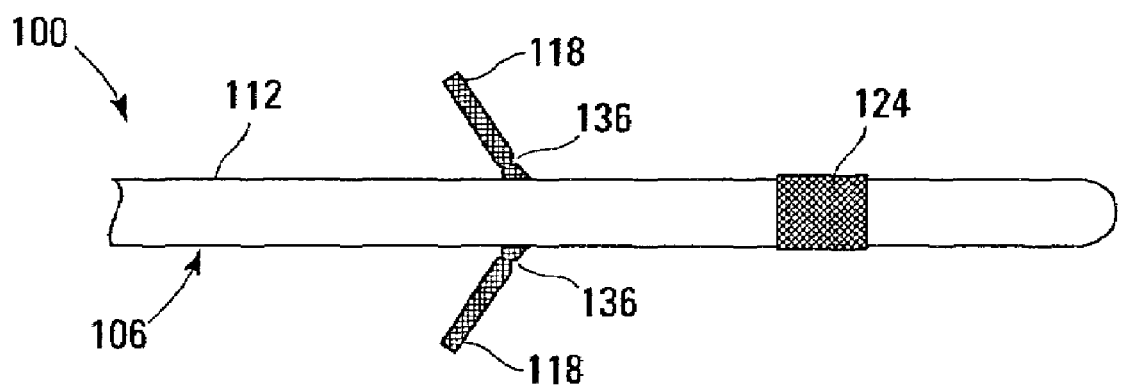
FIG. 2 illustrates a distal end portion of a lead including a fixation feature according to one embodiment of the present invention.

FIG. 2 illustrates a distal end portion of a lead 100 including fixation features according to one embodiment of the present invention. As shown in FIG. 2, the lead 100 includes a lead body 106 having an outer surface 112, a pair of tines 118 extending from the body 106, and a collar 124 on the body 106. The tines 118 and the collar 124 operate as fixation features and are made, in the illustrated embodiment, of a fabric adapted to frictionally engage the inner surface of the target cardiac vessel (e.g., the coronary sinus 31 or the branch vessel 34). In one embodiment, the fabric tines 118 and collar 124 are porous, and the pore size and/or density are strategically controlled so as to create a controlled amount of tissue in-growth for chronic fixation.

In one embodiment, the tines 118 and/or the collar 124 are made substantially entirely from the porous fabric. In another embodiment (not shown), the tines 118 and/or the collar 124 include a base material, which may be the same material (e.g., polyurethane or silicone) used for the lead body, and only tissue contacting outer surfaces are made from or include the porous fabric. In one such embodiment, the tines 118 are formed integrally with the lead body 106 and covered with the porous fabric to form the fixation feature.

In one embodiment, the tines 118 and/or the collar 124 are releasably attached to the lead body 106, such that after tissue in-growth occurs to chronically fix the lead 100 in its implanted position, the tines 118 and/or the collar 124 can be detached from the lead 100 and left behind. In one such embodiment, the tines 118 may include stress points 136 which are adapted to separate upon the application of a sufficient tensile force to the lead body 106 after tissue in-growth occurs. That is, the stress points 136 are configured such that after substantial tissue in-growth, the tines 118 are more weakly attached to the lead body 106 than to the cardiac tissue. In another embodiment, the tines 118 and/or the collar 124 may be attached to the lead body 106 by an adhesive bond that is weaker than the attachment strength of the tines 118 and/or the collar 124 to the cardiac vessel tissue resulting from tissue in-growth. Alternatively, the collar 124 may be frictionally coupled to the lead body 106 using an interference fit designed to be sufficiently strong so as to maintain the fixation feature on the body 106 during delivery of the lead 100, yet allow the lead 100 to be pulled from the collar 124 after the collar 124 has been chronically fixed in place (e.g., due to tissue in-growth). In yet another embodiment, a resorbable adhesive may be used to attach the collar 124 to the lead body 106, which adhesive dissolves over time. In one embodiment, the tines 118 are attached to a ring disposed on the body 106 and releasably attached to the body 106 in, for example, the same manner as the collar 124.

In some embodiments, the collar 124 does not extend entirely circumferentially around the lead body 106. In some embodiments, the collar 124 is provided in the form of a relatively localized fabric patch strategically positioned, based on, for example, a pre-curved portion of the lead 100 such that it will contact the vessel tissue when implanted.

The tines 118 and/or the collar 124 may be strategically located at any tissue contacting portion of the lead 100. For example, the tines 118 and/or collar may be located in a pre-curved portion or in a portion of the lead without any pre-shaped curvature. In addition, in some embodiments, the lead 100 may include multiple pairs of tines 118 and/or multiple collars 124.

The fabric for the tines 118 and/or collar 124 may be made from any biocompatible material and have any structure amenable to controlling pore size in order to control the amount of tissue in-growth into the fabric. In one exemplary embodiment, the tines 118 and/or collar 124 may be made from or include a woven, knitted, or braided fabric made from individual fibers of polyethelene therephthalate (PET, sold under the brand name Dacron™). In such embodiments, interstitial spaces between individual fibers provide macro-pores for tissue in-growth, and the sizes of such pores can be controlled by, for example, the thickness of the individual fibers and the particular structure of the weave, knit, or braid. In some embodiments, the fabric structure can include a porous expanded polytetrafluoroethylene (ePTFE) material having pores selectively controlled in terms of quantity, size, and/or distribution. In one embodiment, a strand or thread of Dacron™ or comparable material is wound around the tines 118 and/or a base ring of the collar 124 to form the tissue engaging outer surface, with the windings configured such that tissue in-growth can occur at the interfaces between the individual threads. Because of the fibrous structure of fiber forms of PET, embodiments utilizing this material will exhibit superior beneficial tissue responses (e.g., endothelialization and tissue in-growth).

Figure 3A:
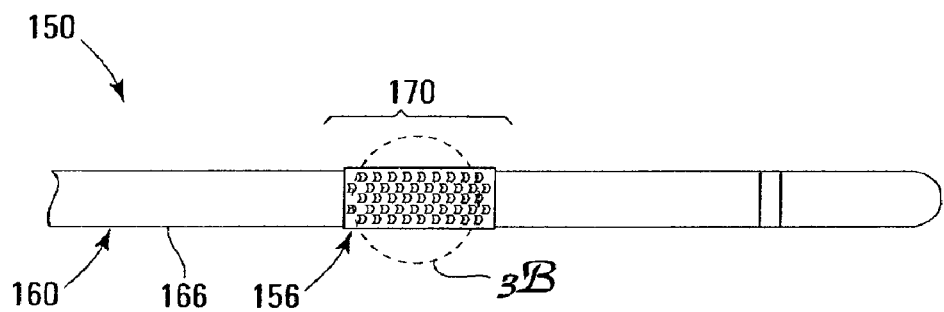
FIGS. 3A-3D illustrate a portion of a lead including a fixation feature according to another embodiment of the present invention.
Figure 3B:
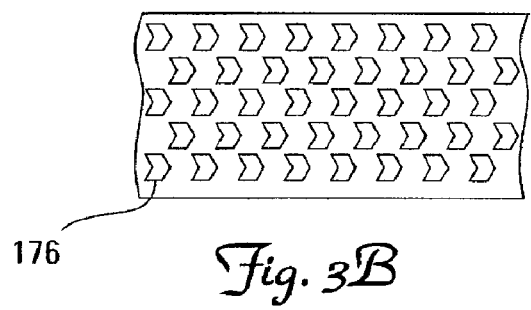

FIGS. 3A-3D illustrate a portion of a lead 150 including a fixation feature 156 according to another embodiment of the present invention. As shown in FIG. 3A, the lead 150 includes a body 160 having an outer surface 166, and a tissue contacting portion 170. The fixation feature 156 is located in the tissue contacting portion 170. As shown in FIG. 3B, the fixation feature 156 includes a plurality of treads 176 on the lead body 160. The treads 176 change the profile of the outer surface 166, and operate to increase frictional drag on the lead body 160. The treads 176 may be arranged randomly as shown in FIG. 4B, or may be arranged in a pattern. In the illustrated embodiment, the individual treads are substantially uniform in size, although in other embodiments, the size, shape, and orientation of the treads 176 may vary.

Figure 3C:
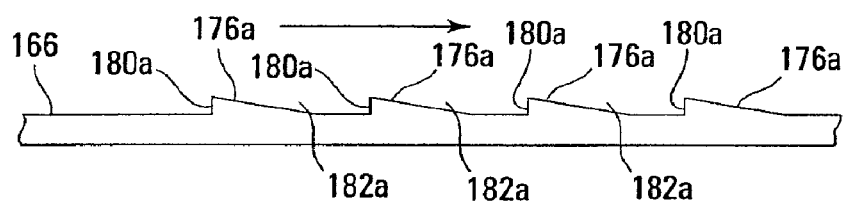
Figure 3D:
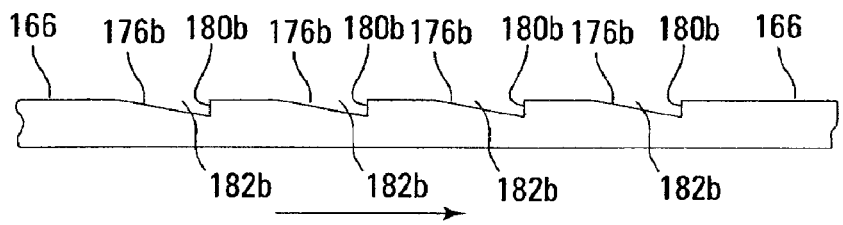

FIGS. 3C and 3D illustrate, schematically, side profiles of alternative embodiments 176a and 176b, respectively, of the treads 176. As shown in FIG. 3C the treads 176a are in the form of ramps configured to permit the lead 150 to preferentially move in the distal direction (as indicated by the arrows in FIG. 3C). As further shown, the treads 176a include surfaces 180a which operate to resist movement of the lead 150 in the proximal direction. In addition, as illustrated, the treads 176a form sites 182a for tissue in-growth. In the embodiment illustrated in FIG. 3C, the treads 176a are disposed on and extend radially beyond the outer surface 166. In the embodiment illustrated in FIG. 3D, the treads 176b are recessed from the lead body outer surface 166. As further shown, the treads 176b are adapted to preferentially permit movement in the distal direction (as indicated by the arrows in FIG. 3D) and include surfaces 180b which operate to resist movement of the lead 150 in the proximal direction. In addition, as illustrated, the treads 176b form sites 182b for tissue in-growth.

In one embodiment, the fixation feature 156 is included on a ring or sleeve disposed on the lead body 160. In one such embodiment, the sleeve may be made detachable from the lead 150 after tissue in-growth occurs in, for example, the manner described above. For example, the sleeve including the fixation feature 156 may be attached to the lead body 160 using an adhesive creating an adhesive bond that is weaker than the attachment strength of the fixation feature 156 to the cardiac vessel tissue due to tissue in-growth, such that a proximally directed force can separate the sleeve from the lead body 160, leaving the sleeve implanted in the cardiac vessel. Alternatively, the fixation feature 156 may be frictionally coupled to the lead body 160 using an interference fit designed to be sufficiently strong so as to maintain the fixation feature on the body 160 during delivery, but yet still allow the lead to be pulled from the sleeve after the sleeve has been chronically fixed in place. In yet another embodiment, a resorbable adhesive may be used to attach the sleeve including the fixation feature 156 to the lead body 106, which adhesive dissolves over time.

The fixation feature 156 may be made from a variety of materials known in the art for use in implantable leads. Exemplary materials include silicone and polyurethane, although other suitable materials will be apparent to those skilled in the art. In one embodiment, the fixation feature 156 is formed integrally with the lead body 160, and thus is made from the same material as the selected portion of the lead body 160.

Figure 4:
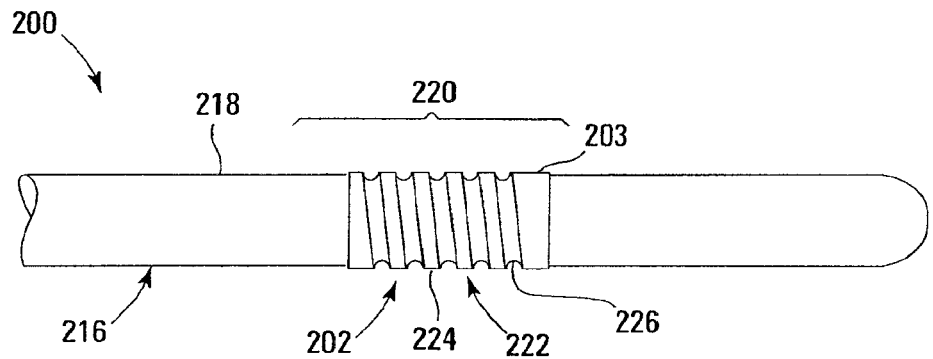
FIGS. 4-5 illustrate portions of leads including fixation features according to additional embodiments of the present invention.

FIG. 4 illustrates a portion of a lead 200 including a fixation feature 202 according to another embodiment of the present invention. As shown in FIG. 4, the lead 200 includes a body 216 having an outer surface 218, and a tissue contacting portion 220 including the fixation feature 202. In the embodiment illustrated in FIG. 4, the fixation feature 202 is a sleeve 203 including a helical groove 222 defined by a helically shaped peripheral surface 224 and a trough 226. As shown in FIG. 4, the trough 226 has a generally semi-circular or rounded profile.

Figure 5:
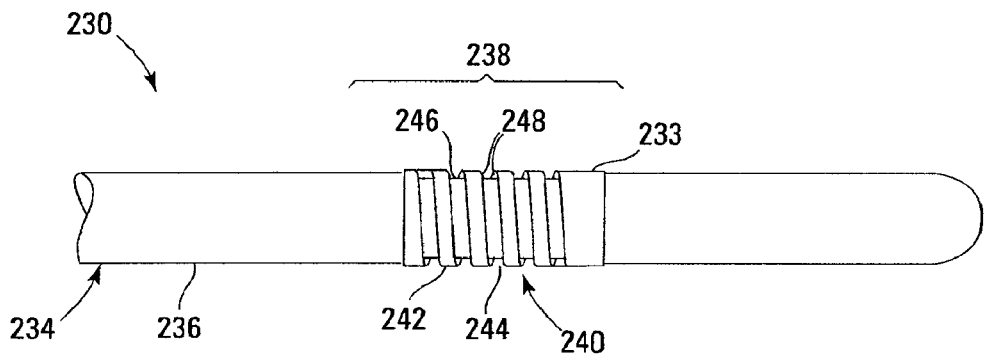

FIG. 5 illustrates a portion of a lead 230 including a fixation feature 232 according to another embodiment of the present invention. As shown in FIG. 5, the lead 230 includes a body 234 having an outer surface 236, and a tissue contacting portion 238 including the fixation feature 232. As illustrated, the fixation feature 232 is a sleeve 233 including a helical groove 240 defined by a helically shaped peripheral surface 242 and a trough 244. As illustrated, the trough 244 has a rectangular profile, defined by a base 246 oriented generally parallel to the peripheral surface 242, and parallel walls 248 extending at substantially right angles from the base 246 to the peripheral surface 242.

Figure 6A:
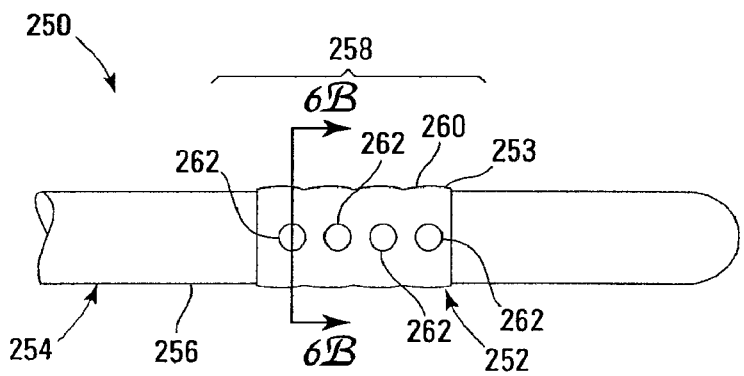
FIGS. 6A-6B illustrate a portion of a lead including a fixation feature according to another embodiments of the present invention.
Figure 6B:
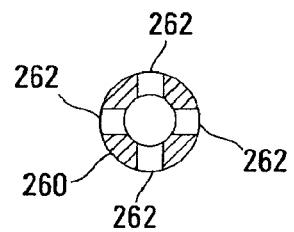

FIGS. 6A and 6B illustrate a portion of a lead 250 including a fixation feature 252 according to another embodiment of the present invention. As shown in FIG. 6A, the lead 230 includes a body 254 having an outer surface 256, and a tissue contacting portion 258 including the fixation feature 252. As illustrated, the fixation feature 252 is a sleeve 253 having a peripheral surface 260 and a plurality of longitudinally spaced apertures 262 extending radially inward from the peripheral surface 260. As shown in FIGS. 6A and 6B, the apertures 262 are arranged in four parallel rows positioned approximately 90 degrees apart about the circumference of the lead 250. In other embodiments (not shown) the apertures 262 may be arranged randomly or in an alternative (e.g., helical) pattern. In another embodiment, there may be fewer or more than four rows of apertures 262.

Figure 7:
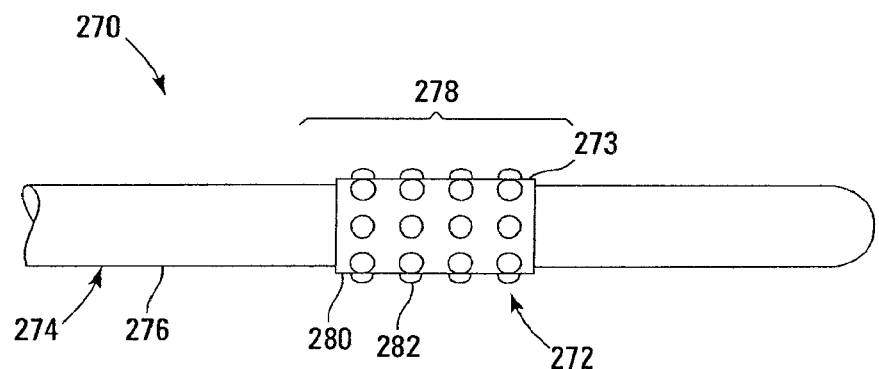
FIG. 7 illustrates a portion of a lead including a fixation feature according to another embodiment of the present invention.

FIG. 7 illustrates a portion of a lead 270 including a fixation feature 272 according to another embodiment of the present invention. As shown in FIG. 7, the lead 270 includes a body 274 having an outer surface 276, and a tissue contacting portion 278 including the fixation feature 272. As shown, the fixation feature 272 is a sleeve 273 having a peripheral surface 280 and a plurality of projections 282 extending radially outwardly from the peripheral surface 280. In the illustrated embodiment, the projections 282 are generally semi-spherical, although in other embodiments (not shown), the projections 282 may have different shapes. Additionally, although the illustrated embodiment includes multiple generally parallel rows of projections 282, in other embodiments (not shown), the projections 282 may be arranged in other patterns, or may be randomly located.

Figures 8A, 8B:
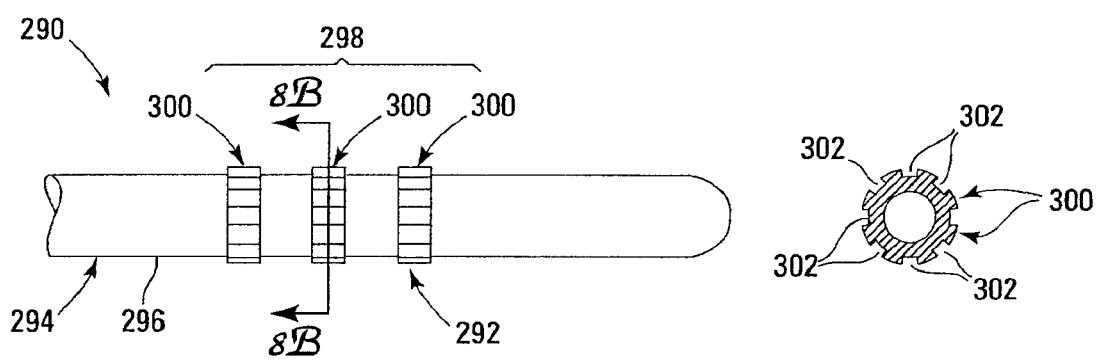
FIGS. 8A-8B illustrate a portion of a lead including a fixation feature according to another embodiment of the present invention.

FIGS. 8A-8B illustrate a portion of a lead 290 including a fixation feature 292 according to another embodiment of the present invention. As shown in FIGS. 8A-8B, the lead 290 includes a body 294 having an outer surface 296, and a tissue contacting portion 298 including the fixation feature 292. As shown, the fixation feature 292 includes a series of longitudinally spaced individual rings 300, each having a plurality of notches 302 at spaced locations about its circumference. In the embodiment illustrated in FIGS. 8A-8B, the fixation feature 292 includes three individual rings 300. In other embodiments (not shown), the fixation feature 292 may include more or fewer than three individual rings 300. Similarly, the individual ring(s) 300 may, in other embodiments, include more or fewer notches 302 than are shown in the embodiment of FIGS. 8A-8B. The rings 300 may be coupled directly to the lead body 296, or may be incorporated into a sleeve disposed over and coupled to the lead body 296.

The fixation features 202, 232, 252, 272, and/or 292 can be releasably coupled to and thus detachable from the respective leads after tissue in-growth occurs to permit repositioning and/or removal of the lead, if desired. For example, any of the sleeves 203, 233, 253, and/or 273, and the rings 300 may be attached to the respective lead body using an adhesive creating an adhesive bond that is weaker than the attachment strength of the fixation feature to the cardiac vessel tissue due to substantial tissue in-growth, such that a proximally directed force can separate the fixation feature from the lead body. As with other embodiments described above, the fixation features could be releasably attached to the respective lead body by a friction or interference fit, or by use of a resorbable adhesive that dissolves over time.

Each of the fixation features 202, 232, 252, 272, and 292 is adapted for engaging the inner surface of the cardiac vessel (e.g., the coronary sinus 31 or the branch vessel 34) for both acute and chronic fixation. The fixation features 202, 232, 252, 272, and 292 are adapted to provide acute fixation of the respective leads by frictionally engaging the cardiac vessel tissue. In addition, the fixation features 202, 232, 252, 272, and 292 include sites (e.g., the troughs 226, 244 of the fixation features 202, 232, and the notches 302 of the fixation feature 292) for tissue in-growth and resulting chronic fixation.

The fixation features 202, 232, 252, 272, and 292 may be made from a variety of materials known in the art for use in implantable medical electrical leads. Exemplary materials include silicone and polyurethane, although other suitable materials will be apparent to those skilled in the art.

Figure 9A:
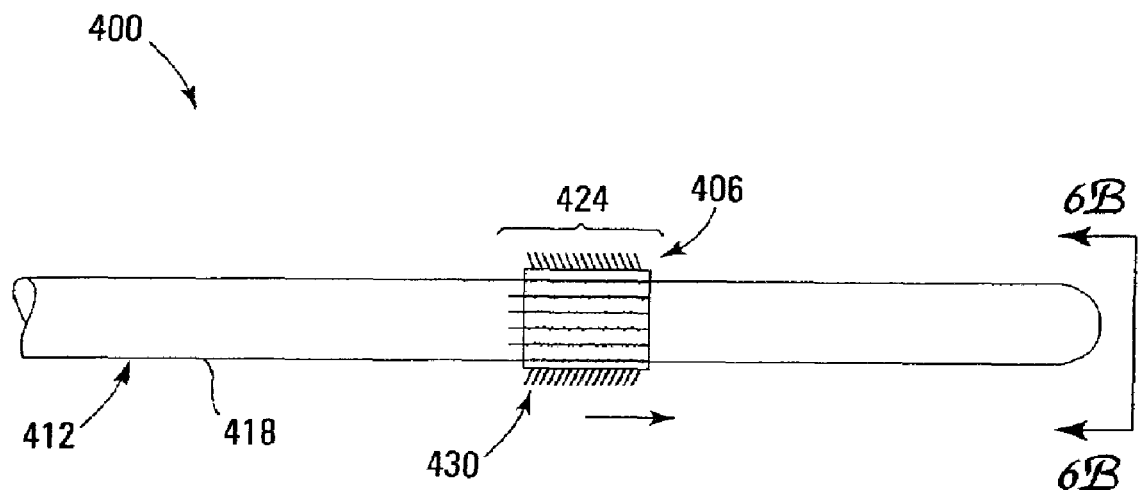
FIGS. 9A-9B illustrate a portion of a lead including a fixation feature according to another embodiment of the present invention.
Figure 9B:
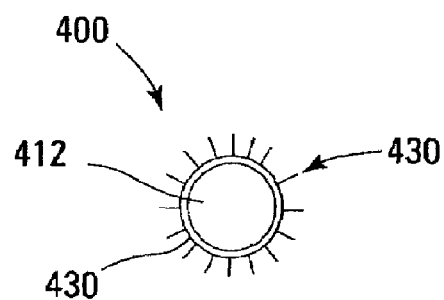

FIGS. 9A and 9B illustrate a portion of a lead 400 including a fixation feature 406 according to another embodiment of the present invention. As shown in FIG. 9A, the lead 400 includes a body 412 having an outer surface 418, and a tissue contacting portion 424. The fixation feature 406 is located in the tissue contacting portion 424, and includes a plurality of filaments 430 forming micro-tines or cilia extending radially outward from the lead body outer surface 418. In the illustrated embodiment, the filaments 430 are oriented to extend at an angle relative to the outer surface 418, such that the filaments 430 preferentially permit movement of the lead 400 in the distal direction (as indicated by the arrow in FIG. 9) and resist movement in the proximal direction. As illustrated, the filaments 430 are shown arranged in rows spaced about the circumference of the lead 400. In other embodiments, the filaments may be randomly positioned on the tissue contacting portion 424.

As with the other fixation features described above, the fixation feature 406 is adapted for engaging the inner surface of the cardiac vessel (e.g., the coronary sinus 31 or the branch vessel 34) for both acute and chronic fixation. The filaments 430 increase the contact surface area between the tissue contacting portion 424 and the cardiac vessel tissue, thereby increasing friction and drag for resisting movement of the lead, particularly in the proximal direction. In addition, the relatively close proximity of the filaments 430 to one another creates sites amenable to tissue in-growth and resulting chronic fixation. The degree of both acute and chronic fixation (e.g., the frictional resistance and/or the attachment strength due to tissue in-growth) can be controlled by controlling, for example, the size, shape, and distribution of the filaments 430, as well as the materials from which the filaments 430 are made.

The filaments 430 may have any of a variety of cross-sectional shapes, such as, for example, cylindrical, tubular, rectangular, square, or elliptical. In one embodiment, the filaments 430 are generally cylindrical with an outside diameter of from about 0.001 inches to about 0.004 inches. In one embodiment, the filaments 430 have an outside diameter of about 0.002 inches. In one embodiment, the filaments 430 are disposed about the lead body 412 at a density selected to create sufficient drag due to frictional engagement with the vessel tissue, thereby resisting spontaneous movement of the lead 400. In one embodiment, the filaments 430 are tightly packed at their bases. In one embodiment, the filaments are spaced apart so as to provide sites for tissue in-growth between the individual filaments. The lengths of the filaments 430 are generally selected so as to ensure contact with the wall of the target vessel in which the lead 430 is partially implanted. In various embodiments, the filaments 430 may vary in length, depending primarily, but not exclusively, on the internal diameter of the target cardiac vessel and the outer diameter of the lead body 412.

In some embodiments, the filaments 430 may be made from a resilient material (e.g., silicone or suture materials). In other embodiments, the filaments 430 are made from more rigid materials such as polyurethane or other semi-rigid polymeric materials. In still other embodiments, the filaments 430 may be made from fine metallic fibers (e.g., stainless steel, Nitinol).

In one embodiment, the fixation feature 406 is formed integrally with the lead body 412. Alternatively, as with other various embodiments described above, the fixation feature 406 as illustrated is included on a ring or sleeve disposed on the lead body 412. In one such embodiment, the sleeve may be made detachable from the lead 400 after substantial tissue in-growth occurs. For example, the sleeve including the fixation feature 406 may be attached to the lead body 412 using an adhesive bond or an interference fit. In these embodiments, the attachment of the sleeve to the lead body 412 is designed to be weaker than the attachment strength of the fixation feature 406 to the cardiac vessel tissue due to tissue in-growth, such that a proximally directed force can separate the sleeve from the lead body 412, leaving the sleeve implanted in the cardiac vessel. Alternatively, as also described above, the sleeve could be coupled to the lead body 412 using a resorbable adhesive that dissolves over a selected period of time (e.g., several months), by which time fibrosis in the vein would be sufficient to hold the lead in place.

The fixation features described herein may be strategically located at any tissue contacting portion of the respective cardiac lead. For example, the fixation features may be located in a pre-curved portion or in a portion of the lead without any pre-shaped curvature. Furthermore, the number of fixation features that can be incorporated into a particular lead is not limited. Additionally, it will be appreciated that a particular lead may incorporate combinations of the various fixation feature embodiments.

Figure 10:
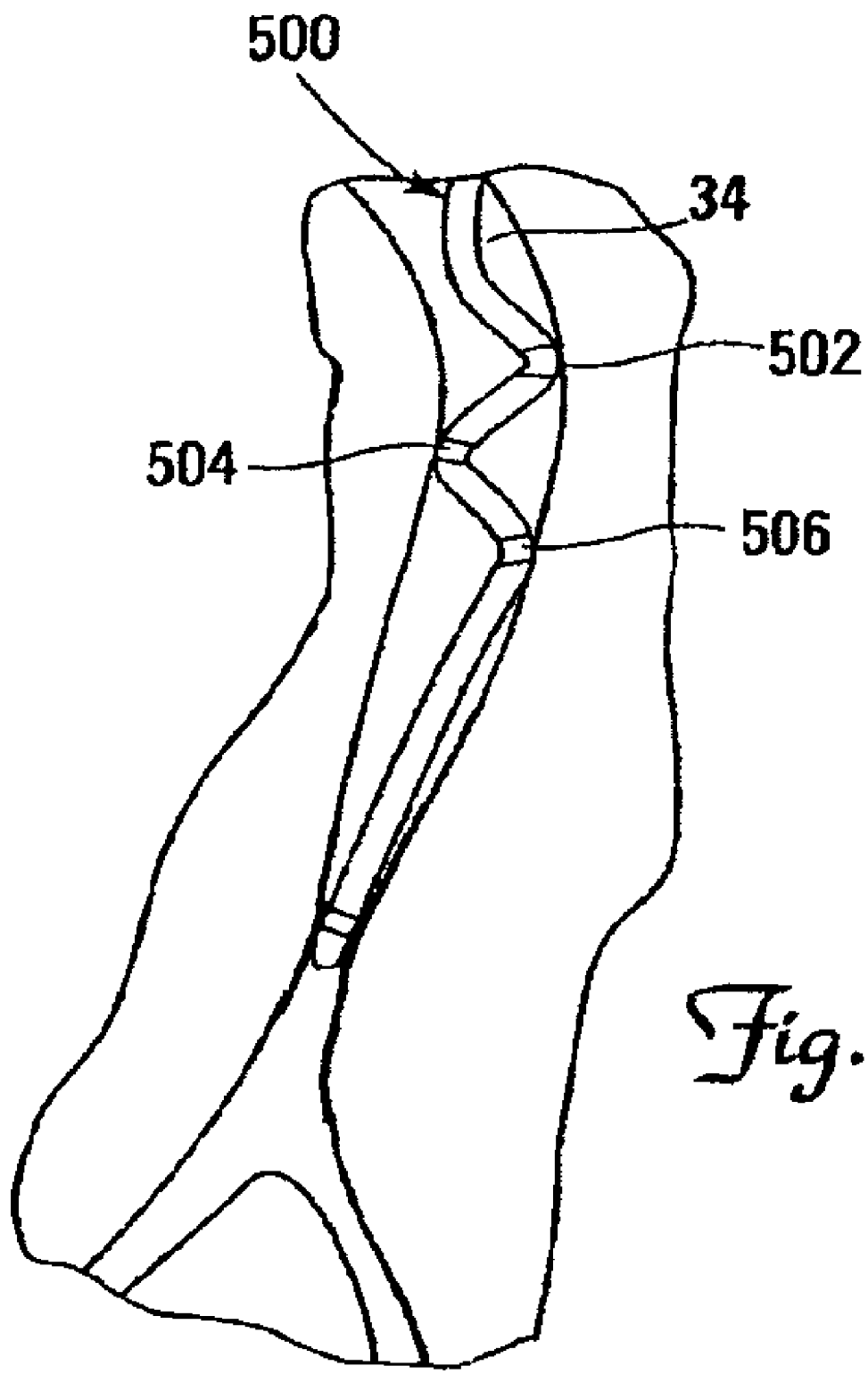
FIG. 10 illustrates a portion of a distal region of an exemplary lead including tissue engaging portions strategically located on the lead and including an exemplary fixation feature according to one embodiment of the present invention.

FIG. 10 shows an exemplary lead 500 having a pre-curved distal end portion 501 partially implanted in the branch vessel 34 (see FIG. 1). In the illustrated embodiment of FIG. 10, the pre-curved distal end portion 501 has a spiral shape and includes tissue engaging portions 502, 504, 506. As is apparent from FIG. 10, the pre-curved distal end portion 501 is configured to urge the tissue contacting portions 502, 504, 506 into contact with the inner surface of the branch vessel 34. The tissue engaging portions 502, 504, 506 further include one or more of the fixation features of the present invention described above for frictionally engaging the inner wall tissue of the vessel 34 and for facilitating tissue in-growth for chronic fixation. It will be appreciated that the fixation features of the present invention can be incorporated onto other pre-curved lead shapes (e.g., J-shapes, sinusoidal shapes). Additionally, the fixation features of the present invention can be disposed at other locations along the respective leads (e.g., along portions positioned within the coronary sinus 31 or great cardiac vein 33, see FIG. 1).

Any or all of the foregoing fixation features may include additional treatments (e.g., coatings) to promote tissue in-growth for chronic fixation. Additionally, the fixation features may include coatings including antibiotic drugs to reduce the potential for infection. In addition, the fixation features may be made of resorbable materials as are known in the art. As will be appreciated, constructing the fixation features of resorbable materials may be particularly advantageous with respect to embodiments in which the fixation feature is adapted to be detachable from the lead and left in the body after the lead is removed.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical electrical lead configured to be partially implanted in a cardiac vessel, the lead comprising:

an elongate body defining a proximal region and a distal region, the proximal region including a proximal end adapted to be connected to an implantable medical device, the distal region including at least one tissue contacting portion selectively located to contact an inner surface of the cardiac vessel when the distal region is located in the cardiac vessel; and a fixation feature coupled to the tissue contacting portion, the fixation feature including a sleeve or collar with a fabric structure thereon adapted to frictionally engage the inner surface of the cardiac vessel and to allow tissue in-growth, the sleeve or collar releasably coupled to an outer surface of the lead body by a bond configured to allow the sleeve or collar to be detached from the lead body in response to a proximally directed force applied to the lead when the lead is secured to the cardiac vessel wall by tissue in-growth.

2. The lead of claim 1 wherein the fabric structure is made substantially from a porous fabric.

3. The lead of claim 1 wherein the fixation feature includes a tine, and wherein the fabric structure covers at least a portion of the tine.

4. The lead of claim 1 wherein the fabric structure includes a plurality of windings of a polyethelene therephthalate fiber, wherein an interface between adjacent windings provides a site for tissue in-growth.

5. A medical electrical lead configured to be partially implanted in a cardiac vessel, the lead comprising:

an elongate body defining a proximal region and a distal region, the proximal region including a proximal end adapted to be connected to an implantable medical device, the distal region including at least one tissue contacting portion selectively located to contact an inner surface of the cardiac vessel when the distal region is located in the cardiac vessel; and fixation means releasably coupled to the lead body in the tissue contacting portion for engaging the cardiac vessel wall and allowing tissue in-growth the fixation means including a sleeve or collar releasably coupled to an outer surface of the lead body by a bond configured to allow the sleeve or collar to be detached from the lead body in response to a proximally directed force applied to the lead when the lead is secured to the cardiac vessel wall by tissue in-growth.

6. The lead of claim 5 wherein the sleeve or collar is coupled to the lead body by an adhesive bond.

7. The lead of claim 5 wherein the sleeve or collar is coupled to the lead body by an interference fit.

8. The lead of claim 5 wherein the fixation means includes a fabric structure.

9. The lead of claim 5 wherein the fixation means includes at least one tine having a tissue engaging surface made substantially from a porous fabric material.

10. The lead of claim 5 wherein the fixation means includes a collar having a tissue engaging surface made substantially from a porous fabric material.

11. The lead of claim 5 wherein the fixation means includes a plurality of tread structures adapted to frictionally resist translation of the lead body in a proximal direction and to preferentially permit translation of the distal portion in a distal direction.

12. The lead of claim 5 wherein the sleeve includes a helical groove defined by a peripheral surface and a trough.

13. The lead of claim 5 wherein the sleeve has a peripheral surface and includes a plurality of apertures extending radially inward from the peripheral surface.

14. The lead of claim 5 wherein the sleeve has a peripheral surface and includes a plurality of projections extending radially outward from the peripheral surface.

15. The lead of claim 14 wherein at least some of the projections are generally semi-spherical in shape.

16. The lead of claim 5 wherein the sleeve has a peripheral surface and includes a plurality of longitudinally spaced rings, the rings including a plurality of notches at spaced locations about a circumference of the respective rings.

17. The lead of claim 5 wherein the fixation feature includes a plurality of filaments extending radially outward from the lead body.

* * * * *